United States Patent [19]

Kanda

[11] Patent Number: 5,065,020
[45] Date of Patent: Nov. 12, 1991

[54] ENERGY DISPERSIVE X-RAY SPECTROMETER

[75] Inventor: Kimio Kanda, Katsuta, Japan

[73] Assignee: Hitachi, Ltd., Tokyo, Japan

[21] Appl. No.: 616,249

[22] Filed: Nov. 20, 1990

[30] Foreign Application Priority Data

Nov. 22, 1989 [JP] Japan ................... 1-302172

[51] Int. Cl.$^5$ .......................................... G01N 23/04
[52] U.S. Cl. ..................................... 250/310; 250/311
[58] Field of Search ............ 250/310, 311, 305, 307, 250/397; 328/45, 49, 82, 100

[56] References Cited

U.S. PATENT DOCUMENTS

| | | | |
|---|---|---|---|
| 4,885,465 | 12/1989 | Nagatsuka et al. | 250/310 |
| 4,894,541 | 1/1990 | Ono | 250/310 |
| 4,988,872 | 1/1991 | Nagatsuka et al. | 250/310 |

OTHER PUBLICATIONS

"Scanning Electron Microanalyzer and X-Ray Microanalysis" Edited by Joseph I. Goldstein et al., 1981, pp. 222-273.

Primary Examiner—Jack I. Berman
Assistant Examiner—Kiet T. Nguyen
Attorney, Agent, or Firm—Antonelli, Terry, Stout & Kraus

[57] ABSTRACT

An energy dispersive X-ray spectrometer used in combination with an electron microscope is disclosed, in which the energy of an electron beam of the electron microscope, with which a sample is irradiated, is determined exactly by detecting the disappearance point of the energy dispersive X-ray spectra on the high energy side, this energy of the irradiation electron beam thus determined being used as a parameter in a calculation for the quantitative energy dispersive X-ray analysis.

9 Claims, 3 Drawing Sheets

FIG. 4

```
┌─────────────────────────────┐
│ READ OUT ACCELERATION       │ 41
│ VOLTAGE SET FOR             │
│ ELECTRON MICROSCOPE         │
└─────────────────────────────┘
              │
┌─────────────────────────────┐
│ CALCULATION VALUE           │ 42
│ CORRESPONDING TO -10%       │
│ OF SET ACCELERATION         │
│ VOLTAGE THUS READ OUT       │
└─────────────────────────────┘
              │
┌─────────────────────────────┐
│ TAKE OUT EDS SAMPLE VALUE   │ 43
│ ($V_A$) CLOSEST TO RESULT OF│
│ -10% CALCULATION            │
└─────────────────────────────┘
              │
┌─────────────────────────────┐
│ CALCULATION VALUE           │ 44
│ CORRESPONDING TO +10%       │
│ OF SET ACCELERATION         │
│ VOLTAGE THUS READ OUT       │
└─────────────────────────────┘
              │
┌─────────────────────────────┐
│ TAKE OUT EDS SAMPLE         │ 45
│ VALUE ($V_B$) CLOSEST       │
│ TO RESULT OF +10%           │
│ CALCULATION                 │
└─────────────────────────────┘
              │
┌─────────────────────────────┐
│ INTEGRATE EDS SPECTRA       │ 46
│ FROM $V_A$ TO $V_B$ TO OBTAIN│
│ INTEGRAL CURVE              │
└─────────────────────────────┘
              │
┌─────────────────────────────┐
│ OBTAIN ENERGY VALUE AT      │ 47
│ INTEGRATION POINT           │
│ CORRESPONDING TO 99% OF     │
│ SATURATION POINT OF INTE-   │
│ GRAL CURVE THUS OBTAIN      │
└─────────────────────────────┘
              │
┌─────────────────────────────┐
│ DETERMINE TRUE ACCELERA-    │ 48
│ TION VOLTAGE OF IRRADIATION │
│ ELECTRON BEAM BY USING      │
│ THIS ENERGY VALUE           │
└─────────────────────────────┘
              │
┌─────────────────────────────┐
│ ADOPT ACCELERATION          │ 49
│ VOLTAGE THUS DETERMINED,    │
│ AS A PARAMETER IN           │
│ CALCULATION FOR             │
│ QUANTITATIVE EDS            │
│ ANALYSIS                    │
└─────────────────────────────┘
```

FIG. 5

```
┌─────────────────────────────┐
│ READ OUT ACCELERATION       │ 51
│ VOLTAGE SET FOR             │
│ ELECTRON MICROSCOPE         │
└─────────────────────────────┘
              │
┌─────────────────────────────┐
│ CALCULATE VALUE CORRES-     │ 52
│ PONDING TO 10% OF SET       │
│ ACCELERATION VOLTAGE        │
│ THUS READ OUT               │
└─────────────────────────────┘
              │
┌─────────────────────────────┐
│ TAKE OUT EDS SAMPLE         │ 53
│ VALUE ($V_A$) CLOSEST       │
│ TO RESULT OF -10%           │
│ CALCULATION                 │
└─────────────────────────────┘
              │
┌─────────────────────────────┐
│ OBTAIN VALUE, WHICH IS      │ 54
│ 1/2 OF HEIGHT OF EDS        │
│ SPECTRA AT $V_A$            │
└─────────────────────────────┘
              │
┌─────────────────────────────┐
│ OBTAIN HEIGHEST             │ 55
│ ENERGY IN EDS               │
│ SPECTRA ABOVE               │
│ THIS 1/2 VALUE              │
└─────────────────────────────┘
              │
┌─────────────────────────────┐
│ DETERMINE TRUE ACCELERA-    │ 56
│ TION VOLTAGE OF IRRADIATION │
│ ELECTRON BEAM BY USING      │
│ THIS ENERGY VALUE           │
└─────────────────────────────┘
              │
┌─────────────────────────────┐
│ ADOPT ACCELERATION          │ 57
│ VOLTAGE THUS DETERMINED     │
│ AS A PARAMETER IN           │
│ CALCULATION FOR             │
│ QUANTITATIVE EDS            │
│ ANALYSIS                    │
└─────────────────────────────┘
```

ENERGY DISPERSIVE X-RAY SPECTROMETER

BACKGROUND OF THE INVENTION

The present invention relates to an energy dispersive X-ray spectrometer (hereinbelow abbreviated to EDS), and in particular to an energy dispersive X-ray spectrometer used by combining it with an electron microscope such as a transmission electron microscope, a scanning electron microscope, an electron probe microanalyzer, etc.

Heretofore the EDS is used often by combining it with an electron microscope (including a transmission electron microscope, a scanning electron microscope, etc.) and utilized for element analysis of a specimen or sample image observed by using an electron microscope. This element analysis can be classified roughly into the qualitive analysis, by which what elements are contained is studied, and the quantitative analysis, by which what elements are contained and how much they are contained are studied. The qualitative analysis can be effected relatively easily, because the elements are only identified on the basis of the position of peaks in a spectrum. On the contrary, the quantitative analysis cannot be effected always easily, because the quantity thereof is calculated by substituting parameters in complicated formulas including various factors by experimental values obtained under different conditions and therefore various factors are entangled therein. The EDS analysis executed by combining it with an electron microscope is described in "Scanning Electron Microanalyzer and X-ray Microanalysis" edited by Joseph I. Goldstein, et al., 1981, pp. 222-273.

As an important cause producing analysis errors in the prior art techniques described above, in particularly in the quantitative analysis, it can be cited that errors in the energy of the electron beam, with which the sample is irradiated, are great. This occurs by the fact that the value set for the acceleration voltage on the EM side is used for the EDS analysis as it is. That is, formulas including various parameters are used for the quantitative EDS analysis and the set value of the acceleration voltage for the electron beam used in the electron microscope is used as one of the parameters in this formulas. Although the acceleration voltage is set at a certain value, e.g. 100 kV, because of errors in the adjustment of the EM device, the acceleration voltage of the electron beam used for the irradiation is not always 100.00 kV. For example, for an electron microscope it is 100.23 kV and for another it is 99.88 kV. For this reason, heretofore there was a problem that since the set value, which is no real acceleration voltage, is substituted in the formulas stated above as the acceleration voltage, errors are produced in the result of the quantitative analysis.

SUMMARY OF THE INVENTION

The object of the present invention is to provide an EDS, which can detect exactly the energy of the electron beam, with which the sample is irradiated, and effect a quantitative analysis with a high precision in an EDS analysis used, combined with an EM by introducing the energy thus detected in the EDS analysis.

Differing from the wavelength dispersive X-ray spectrometer (hereinbelow abbreviated to WDS) using an analyzing crystal, the EDS can detect not only characteristic X-ray but also continuous X-ray produced by the sample irradiated with the electron beam with a high efficiency. This is a serious demerit of the EDS with respect to the WDS. However, a merit can be obtained that the energy of the electron beam, with which the sample is irradiated, can be detected exactly, if this demerit is utilized usefully. That is, since the energy of the produced continuous X-ray is secondary generated energy generated by shock of the electron beam, it extends from 0 eV to an energy corresponding to the energy of the irradiation electron beam and no X-ray having an energy higher than that of the irradiation electron beam. Consequently the X-ray disappears stepwise at the energy corresponding to the acceleration voltage on the EM side. When the value of the energy disappearing stepwise is monitored, it represents the energy of the electron beam, with which the sample is irradiated. That is, the true set acceleration voltage on the EM side is detected correctly.

In order to achieve the above object, according to the present invention, by using the principle described above, the energy of the electron beam, with which the sample is irradiated, can be detected exactly, and the energy is introduced in the formulas for the EDS analysis.

Since the spectrum of the continuous X-ray in the X-ray detected by the EDS (characteristic X-ray and continuous X-ray) disappears stepwise at the energy corresponding to that of the electron beam, with which the sample is irradiated, it is sufficient to detect exactly this disappearance point, i.e. the disappearing edge. It can be easily detected e.g. by integrating the spectrum of the continuous X-ray at the neighborhood of the energy corresponding to the set acceleration voltage on the EM side. Supposing that the set acceleration voltage on the EM side is 100 kV, it is sufficient to integrate the spectrum of the continuous X-ray e.g. from an energy of 90 kV towards higher energies, e.g. up to an energy of 110 kV and to adopt a point of e..g 99% of the saturation point of the integral value as the irradiation electron energy.

In this way it is possible to detect the energy of the electron beam, with which the sample is irradiated and to effect the quantitative EDS analysis with a high precision by introducing this value in the parameters for the EDS analysis, in particular the quantitative analysis.

BRIEF DESCRIPTION OF THE DRAWINGS

FIG. 4 is a flowchart indicating a procedure for obtaining exactly the acceleration voltage of the irradiation electron beam according to the present invention; and FIG. 5 is a flowchart indicating another procedure for obtaining the acceleration voltage of the irradiation electron beam.

DESCRIPTION OF THE PREFERRED EMBODIMENTS

Figure 1:
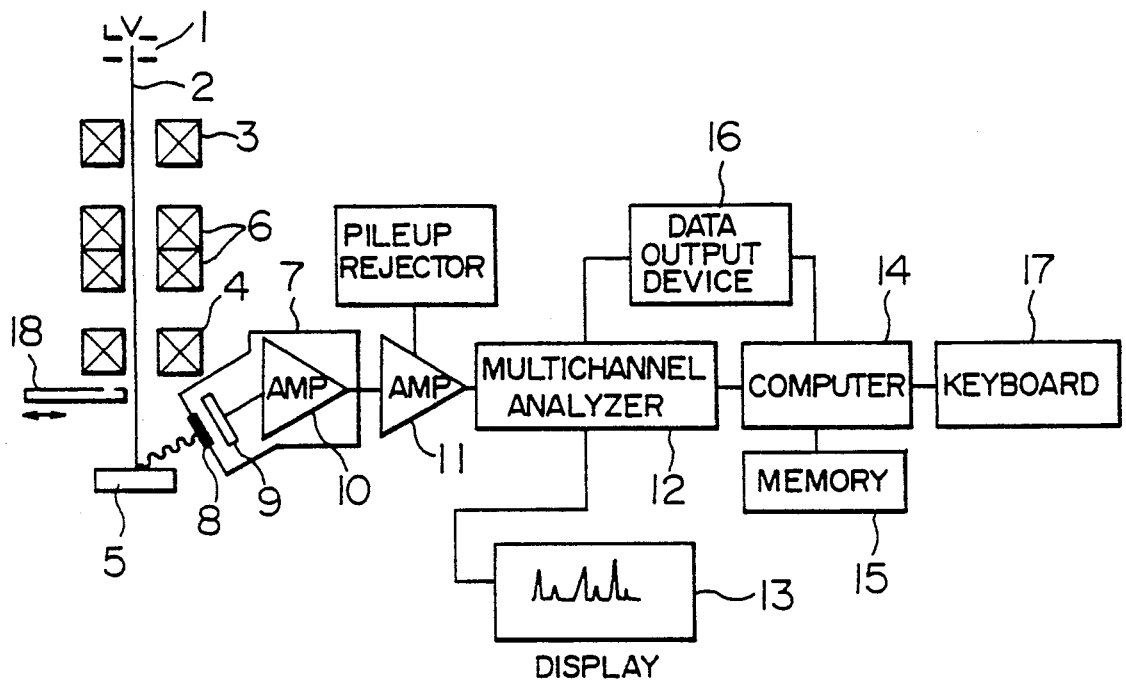
FIG. 1 is a scheme showing the construction of an embodiment of the present invention.

Hereinbelow an embodiment of the present invention will be explained, referring to the drawings.

FIG. 1 shows an example of the whole construction of a scanning electron microscope (hereinbelow abbreviated to SEM) combined with an EDS. An electron beam 2 emitted by an electron gun (wolfram hairpin filament type, $LaB_6$ filament type, FE filament type, etc.) is focused into a fine beam by means of a focusing lens 3 and an objective lens 4 and projected to a sample 5. When an image such as SEM image, X-ray image, etc. is obtained, the sample 5 is scanned with the electron beam 2 by means of a deflection coil 6.

X-rays emitted by the sample are detected by an EDS detector 7. That is, the X-rays are detected by a lithium-drifted silicon detector 9 through a thin type berrylium window 8. Each X-ray is transformed into a voltage pulse by a charge-sensitive preamplifier 10 and amplified and shaped in a pulse by a main amplifier 11 to be supplied to a multi-channel analyzer 12. Voltage pulses thus obtained are discriminated in the pulse height according to the voltage height. The voltage distribution after the discrimination is displayed on a display device 13.

The voltage distribution obtained by discriminating the voltage by means of the multi-channel analyzer 12 is introduced in a computer 14, where processing such as peak identification or quantification is effected further, and stored in a memory 15. 16 represents a data output device for outputting data to the exterior. Further, an operation console such as a keyboard 17 is disposed, which enlarges or reduces the EDS spectra analyzed by the computer 14 and stored in the memory 15, or instructs the qualitative or quantitative analysis thereof.

Further the intensity of the electron beam 2, with which the sample 5 is irradiated, is monitored exactly by using a Faraday cup 18, which can be taken in and out.

Figure 2:
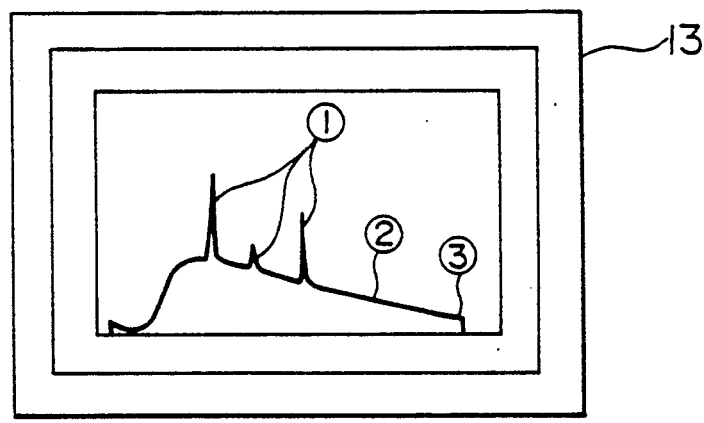
FIG. 2 shows an example of display of the X-ray spectrum displayed on an EDS spectrum display device indicated in FIG. 1.

FIG. 2 shows an example of the X-ray spectrum displayed on the EDS spectrum display device 13. The EDS spectra consists of a part ② indicating the continuous X-ray having a shape of the back of a whole and a part ① indicating characteristic X-rays having sharp peaks displayed so as to be superposed thereon. The higher energy side of the continuous X-ray disappears at the energy ③ corresponding to the energy of the electron ban 2, with which the sample 5 is irradiated.

Figure 3:
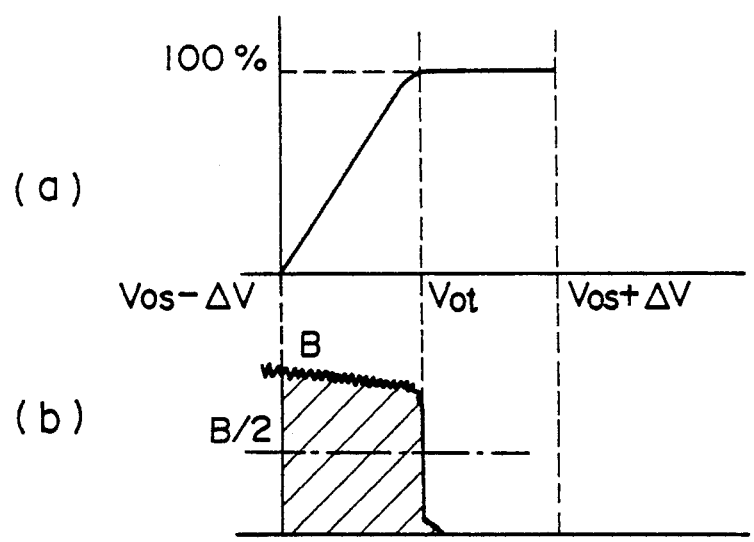
FIG. 3 shows an enlarged spectrum in the neighborhood of the disappearance point of the X-ray spectrum indicated in FIG. 2 and an integral curve of the spectrum.

FIG. 3 shows an enlarged neighborhood of the disappearance point stated above of the X-ray spectra indicated in FIG. 2 (FIG. 3(b)) and an integral curve obtained by integrating the spectra in the neighborhood thereof (FIG. 3(a)), which are made correspond to each other.

The energy $V_{to}$ of the electron beam 2, with which the sample 5 is irradiated, may be obtained from the X-ray spectra obtained in the EDS analysis in the following way. Since the acceleration voltage $V_{os}$ set on the SEM side has an error (usually smaller than ±3%) with respect to the correct value $V_{to}$, the obtained X-ray spectrum is integrated from an energy $V_{os}-\Delta V$ (usually $\Delta V$ is set at 10% of $V_{os}$) towards the higher energy side to $V_{os}+\Delta V$. The disappearance point of the X-ray spectrum is no ideally stepwise disappearance point because of fluctuations in the energy of the irradiation electron beam 2 (usually smaller than 2 eV) and influences of the inelastic scattering of the electron beam 2 by the sample 5. However, if the center thereof is obtained correctly, this value represents the correct energy $V_{to}$ of the electron beam 2, with which the sample is irradiated. A certain energy (usually about 99% by experience) with respect to the saturation point of the integral curve is $V_{to}$. A computer of minicomputer class is incorporated in the EDS so that various sorts of processings including the qualitative and the quantitative analysis can be effected by means thereof. The formation of the integral curve and the operation of obtaining $V_{to}$ by using it can be executed easily by storing previously a program defining the procedure for executing it in the memory 15 and by following the procedure. Hereinbelow the execution procedure will be explained, referring to FIG. 4.

In FIG. 4, the acceleration voltage set for the electron microscope is read out from the electron microscope side through the computer 14 and stored in the memory 13 (Step 41). The value corresponding to −10% of the read out set acceleration voltage is calculated (Step 42) and the energy value $V_A$ of the EDS spectrum, which is closed to the result of the calculation, is selected and read out from the EDS spectrum stored in the memory 13 (Step 43). Next the value corresponding to +10% of the read out set acceleration voltage is calculated (Step 44) and the energy value $V_B$ of the EDS spectrum, which is closed to the result of the calculation, is selected and read out from the EDS spectrum stored in the memory 13 (Step 45). The EDS spectrum stored in the memory 13 is integrated from $V_A$ to $V_B$ by using the results obtained in Steps 43 and 45 to obtain an integral curve (FIG. 3(a)) (Step 46). The value corresponding to 99% of the saturation point of the integral curve is calculated and the point corresponding to the calculated value on the integral curve is obtained. Then the energy value at that obtained point is obtained (Step 47). The true acceleration voltage is determined by using this energy value thus obtained (Step 48). The acceleration voltage determined in this way is adopted as the acceleration voltage of the irradiation electron beam in the calculation for the quantitative EDS analysis.

As a method for obtaining $V_{ot}$ in a simple manner, a threshold line is drawn at a half value B/2 of the value B of the X-ray spectrum at the point of $V_{os}-\Delta V$ (refer to FIG. 3(b)) and the intersection of this line with the stepwise disappearing curve of the X-ray spectrum may be adopted as $V_{to}$. This method will be explained, referring to FIG. 5.

In FIG. 5, the content of Steps 51 to 53 is identical to that explained, referring to FIG. 4. Next the value, which is ½ of the height of the EDS spectrum at the obtained EDS sample value $V_A$, is obtained (Step 54). Then the highest energy is obtained in the EDS spectrum value above the value of ½ (Step 55). The true acceleration voltage of the irradiation electron beam is determined by using the highest energy thus obtained (Step 56) and the acceleration voltage thus determined is adopted as the parameter for the acceleration voltage in the calculation for the quantitative EDS analysis (Step 57).

The requirement for the precision in the recent quantitative EDS analysis becomes severer and analysis errors of 1 to 2% are required. Consequently, if the acceleration voltage is wrong by 3%, this gives rise directly to analysis errors of several %, which is a serious problem. Taking such a problem into account, the present invention provides a method for obtaining the correct energy $V_{to}$ of the irradiation electron beam.

According to the present invention, since it is possible to obtain the correct energy of the electron beam, with which the sample is irradiated, and to utilize it for obtaining the acceleration voltage of the EM for the EDS analysis, an effect is obtained that the EDS analysis can be effected with a high precision.

I claim:

1. An energy dispersive X-ray spectrometer comprising:
   an electron microscope forming a sample image by irradiating a sample with a predetermined electron beam;
   means for detecting X-rays produced when the sample is irradiated with the electron beam in said electron microscope to convert them into electric signals;
   means for discriminating said signals coming from the detecting and converting means according to the magnitude thereof to form an energy dispersive X-ray spectra;
   means for obtaining the value of the energy, at which the spectra obtained by said spectra forming means disappears substantially on the high energy side; and
   means for using the energy obtained by said energy obtaining means as the energy of the irradiation electron beam in parameters used in a calculation for a quantitative energy dispersive X-ray analysis.

2. An energy dispersive X-ray spectrometer according to claim 1, wherein said electron microscope is a transmission electron microscope.

3. An energy dispersive X-ray spectrometer according to claim 1, wherein said electron microscope is a scanning electron microscope.

4. An energy dispersive X-ray spectrometer according to claim 1, wherein said electron microscope is an electron prove microanalyzer.

5. An energy dispersive X-ray spectrometer according to claim 1, wherein said energy obtaining means is provided with:
   means for reading out the acceleration voltage set for said electron microscope;
   means for integrating said spectra from an energy, which is lower than the set acceleration voltage read out by said reading out means by an amount determined by a predetermined ratio to an energy, which is higher than the set acceleration voltage by an amount determined by the predetermined ratio; and
   means for obtaining a value of the energy at a point, which is lower than the saturation value of the integral value obtained by said integrating means by an amount determined by another predetermined ratio as the energy, at which the spectrum disappears.

6. An energy dispersive X-ray spectrometer according to claim 5, wherein said integrating means is provided with:
   means for obtaining the energy, which is lower than said set acceleration voltage thus read out by an amount determined by the predetermined ratio;
   means for obtaining the energy, which is higher than said set acceleration voltage by an amount determined by the predetermined ratio; and
   means for integrating said spectra from an energy corresponding to said lower energy value to an energy corresponding to said higher energy value to obtain an integral curve.

7. An energy dispersive X-ray spectrometer according to claim 6, wherein said predetermined ratio is 10%.

8. An energy dispersive X-ray spectrometer according to claim 5, wherein said means for obtaining said energy, at which the spectrum disappears, is means for obtaining an energy, at which the integral value is a value of 99% of the saturation value.

9. An energy dispersive X-ray spectrometer according to claim 1, wherein said energy obtaining means is provided with:
   means for reading out the acceleration voltage set for said electron microscope;
   means for obtaining the energy, which is lower than said set acceleration voltage thus read out by an amount determined by the predetermined ratio;
   means for obtaining a value, which is equal to $\frac{1}{2}$ of the spectrum value corresponding to the energy obtained by said means for obtaining said lower energy; and
   means for obtaining the highest energy in the spectra above said value, which is equal to $\frac{1}{2}$ of the spectrum value, for the energy, at which the spectrum disappears.

* * * * *